(12) United States Patent
Viken

(10) Patent No.: US 6,330,934 B1
(45) Date of Patent: *Dec. 18, 2001

(54) COMPLETE FLUID EXCHANGE SYSTEM FOR AUTOMATIC TRANSMISSIONS

(76) Inventor: James P. Viken, 9890 Crestwood Ter., Eden Prairie, MN (US) 55347

( * ) Notice: Subject to any disclaimer, the term of this patent is extended or adjusted under 35 U.S.C. 154(b) by 0 days.

This patent is subject to a terminal disclaimer.

(21) Appl. No.: 08/772,836

(22) Filed: Dec. 24, 1996

Related U.S. Application Data (63) Continuation-in-part of application No. 08/209,261, filed on Mar. 16, 1994, now Pat. No. 5,789,152, which is a continuation-in-part of application No. 07/781,322, filed on Oct. 23, 1991, now Pat. No. 5,318,080.

(51) Int. Cl.$^7$ ..................................................... F16N 33/00
(52) U.S. Cl. ............................... 184/1.5; 184/6.4; 141/67; 141/94; 141/98; 141/65
(58) Field of Search .......................... 184/1.5, 6.4, 104.3, 184/108; 123/196 R; 141/65, 67, 94, 98

(56) References Cited

U.S. PATENT DOCUMENTS

| | | |
|---|---|---|
| 1,829,173 | 10/1931 | Wertz . |
| 3,033,311 * | 5/1962 | Edgar et al. ........................... 184/1.5 |
| 3,447,636 | 6/1969 | Bonfilio . |
| 3,513,941 | 5/1970 | Becnel . |
| 4,745,989 | 5/1988 | DiMatteo . |
| 4,869,346 | 9/1989 | Nelson . |
| 5,015,301 | 5/1991 | Baylor et al. . |
| 5,289,837 | 3/1994 | Betancourt . |
| 5,291,968 | 3/1994 | Brown . |
| 5,318,080 | 6/1994 | Viken . |
| 5,337,708 | 8/1994 | Chen . |
| 5,361,870 | 11/1994 | Courcy . |
| 5,370,160 | 12/1994 | Parker . |
| 5,415,247 * | 5/1995 | Knorr ..................................... 184/1.5 |
| 5,427,202 * | 6/1995 | Behring et al. ........................ 184/1.5 |
| 5,447,184 * | 9/1995 | Betancourt ............................ 184/1.5 |
| 5,482,062 | 1/1996 | Chen . |
| 5,535,849 | 7/1996 | Few . |
| 5,626,170 | 5/1997 | Parker . |

FOREIGN PATENT DOCUMENTS

| | | |
|---|---|---|
| S62-22718 | 5/1986 | (JP) . |
| 2-72299 | 3/1990 | (JP) . |

* cited by examiner

Primary Examiner—Christopher Verdier
(74) Attorney, Agent, or Firm—Larkin Hoffman Daly & Lindgren, Ltd.; John F. Klos (57) ABSTRACT

An improved system for changing the fluid of vehicular automatic transmissions and the like, which has the capability to provide a complete fluid exchange faster and with less usage of fresh fluid in a manner that is easier to operate. This is accomplished by the system's unique capability to extract used fluid and replace it with fresh fluid at a faster, balanced rate than before possible in prior art. This is accomplished by decreasing or removing restriction from the exhausting of the used fluid and introducing fresh fluid at more than one locus. The unique, novel capability of the invention to use a dual use pan access tube to combine a static change with a dynamic change, and to introduce fresh fluid into the transmission from two different loci instead of one as in all prior art, allows the fluid exchange to be completed in a shorter time with less use of fluid. These improvements increase the commercial utility and value of complete fluid changing in automatic transmissions and should extend its commercial viability as a routine maintenance procedure in the vehicular or automotive industry.

35 Claims, 3 Drawing Sheets

COMPLETE FLUID EXCHANGE SYSTEM FOR AUTOMATIC TRANSMISSIONS

This application is a continuation-in-part of application Ser. No. 08/209,261 filed Mar. 16, 1994, now granted U.S. Pat. No. 5,789,152, and now U.S. Reissue Pat. No. RE36,650, which was a continuation-in-part of application Ser. No. 07/781,322 filed Oct. 23, 1991, and now U.S. Pat. No. 5,318,080.

FEDERAL SPONSORSHIP

This invention is not made under any Federally sponsored research or under any other independently sponsored research and development program.

FIELD OF THE INVENTION

This invention relates generally to changing the fluid of vehicular automatic transmissions and more specifically to a complete static and dynamic combination of fluid flushing, purging, cleaning and replacement of used transmission fluid with fresh fluid to the torque convertor, other typically inaccessible transmission components, and the transmission as a whole.

OBJECTS AND ADVANTAGES

The new invention comprehensively coordinates the utilization of both static and dynamic fluid changing in a unique manner as a combined means to effectively institute a Complete Fluid Exchange in the least amount of time practical without harming the transmission or vehicle and with the least use of fresh fluid feasible. These objects have significant commercial value.

Prior art in the area of dynamic fluid changing in automatic transmissions has been problematic in several serious ways that have limited the commercial viability of its use in every day automotive and vehicular preventative maintenance. Previous devices have been difficult to connect in proper alignment to the vehicle, slow to operate, and tend to be wasteful by using too much fresh fluid due to dilution losses. Such devices tend to cause fluid starvation or overpressurization problems in the transmission, with the exception of Viken (U.S. Pat. No. 5,318,080, Issued Jun. 7, 1994).

Viken's device, although not harmful to the vehicle was not convenient for the operator. The primary objects of my invention are to institute a Complete Fluid Exchange in less time, with less fresh fluid sacrificed to unnecessary dilution losses, with minimal complexity in operating the device including minimal difficulty connecting the device to the vehicle being serviced, and with no overpressurization, overfilling or fluid starvation conditions resulting.

This invention has the capabilities to accomplish these objects by use of a unique Pan Access Tube used in combination with a two part fluid changing process comprised of a static fluid change and a dynamic fluid change.

During the static part of the Complete Fluid Exchange this invention utilizes a unique two part flushing and purging of areas that can be reached with the invention. The first part is comprised of flushing and purging used fluid out of the cooling line and its downstream transmission components into the transmission pan. The second part is comprised of the extraction of that purged fluid out of the transmission pan by use of the Pan Access Tube.

During the static part of the Complete Fluid Exchange used fluid which has been forced into the pan is extracted by use of an auxiliary pump in combination with a Pan Access Tube which has been inserted down into the bottom of the transmission pan through the dipstick-filler tube.

The net result of this art is that less fresh fluid is sacrificed to dilution losses. In some cases this reduction approaches 50% of the fresh fluid used. The time necessary for the Fluid Exchange is decreased using this art.

In both embodiments of this invention fresh fluid is not only introduced into the transmission through its cooling return line during the static part of the Complete Fluid Exchange but also during the dynamic part of the Complete Fluid Exchange.

However, in the second and preferred embodiment, fresh fluid is introduced into the transmission at two loci at the same time simultaneously to balance its rate of flow with the used fluid being exhausted from the opened cooling circuit with minimal or no resistance applied, the net result being a Complete Fluid Exchange in a shorter period of time.

Three important objects are obtained by using the Pan Access Tube to introduce fresh fluid directly into the transmission pan in combination and coordination with the introduction of fresh fluid into the cooling return line during the dynamic part of the Complete Fluid Exchange, while removing as much restriction as practical from the extraction means for used fluid. These objects consist of: 1—The static and dynamic parts of the Complete Fluid Exchange are completed in shorter periods of time; 2—Less fresh fluid is used to provide a Complete Fluid Exchange than otherwise possible holding all other factors equivalent; 3—The Complete Fluid Exchange is instituted without damaging the transmission or vehicle in any fashion due to overpressurizing the transmission, overfilling it, or creating any type of fluid starvation condition which could result in scoring and/or erosion of internal transmission components.

Another object of the use of the Pan Access Tube is to increase the rate of introduction of fresh fluid into the transmission to match the greater rate at which used fluid is extracted when increased low pressure is applied by the invention to the outlet side of the opened cooling circuit during the dynamic part of the Complete Fluid Exchange.

The invention has the capability to maintain an overall, ongoing balance between the rate of fresh fluid introduced to the rate of used fluid extracted during the dynamic part of the Complete Fluid Exchange. Because most or all restriction means are removed from the extraction of used fluid from the outlet side of the opened cooling circuit, the Fluid Exchange procedure is significantly speeded up by use of this invention over the prior art.

The unobvious and novel dual use of the Pan Access Tube featured in this invention provides a means to extract used fluid present in the pan when the transmission is static in the first and second embodiments. But, it is also utilized to directly introduce clean fluid into the pan during the last part of the static fluid exchange and through the whole dynamic fluid exchange in the second and preferred embodiment.

The static part of the Complete Fluid Exchange is an initial part of the Complete Fluid Exchange and is in fact a partial fluid change because only certain parts of the transmission can be flushed, purged and refilled when the transmission is not operating. But the use of the static exchange procedure prior to and comprehensively coordinated with a subsequent dynamic exchange can offer a never before available means of shortening the length of time required for the Complete Fluid Exchange and can significantly decrease the overall amount of fresh fluid utilized.

Use of a static fluid exchange before, in addition to, and in coordination with a dynamic fluid exchange allows a total exchange of all used fluid for fresh fluid using the least amount of fresh fluid feasible to attain the same effective results in the least amount of time practical, holding all other factors equivalent.

Useful, unobvious objects attained by use of this invention include but are not limited to increased speed, ease and totality of the Fluid Exchange provided by the Complete Fluid Exchange. Increased efficiency is obtained by using the minimum amount of fresh fluid feasible to obtain the desired, effective results in the minimum amount of time, in as simple a manner as possible without any damage to the vehicle or the transmission.

For these reasons this invention can provide numerous commercial, technical, and consumer/customer benefits to the automotive maintenance industry.

Further objects and advantages of my invention will become apparent from a consideration of the drawings and ensuing description.

SUMMARY OF THE INVENTION

The new invention utilizes an external pumping means as did Viken's invention specified in U.S. Pat. No. 5,318,080 (Issued Jun. 7, 1994) in both embodiments. But, in its preferred second embodiment, the external pumping system for fresh fluid is quite novel when compared to all other prior art since it is bifurcated into two separate but coordinated sources of introducing fresh fluid into the transmission. These two separate but coordinated supply sources can be used to introduce fresh fluid into the transmission at two separate loci at any overall rate needed to match the unrestricted or enhanced exhausting of used fluid specified in the second preferred embodiment.

The invention introduces fresh fluid into the transmission through the cooling return line and this is used in both of its two embodiments during both the static part of the Complete Fluid Exchange and during the dynamic part as well. The invention introduces fresh fluid directly into the transmission pan through the dipstick/filler tube by means of the Pan Access Tube during the static part of the Complete Fluid Exchange in the second embodiment, and during the Dynamic part of the Complete Fluid Exchange in the second embodiment. The Fresh fluid introduced into the transmission from both sources is metered together, that is, measured additively, and both are suitably regulated individually and together by utilizing a variable flow regulator valve and an adjustable relief valve used as a distribution proportioning valve. Of course many other equivalent means can be used without departing from the art.

In order to maintain overall balance between the rate at which used fluid is extracted and the rate at which fresh fluid is introduced during the dynamic part of the complete fluid exchange, fresh fluid must enter the transmission just as fast as the used fluid flows out of the opened cooling line which has had additional low pressure applied to its cooling outlet side in the second, preferred embodiment.

Lack of inclusion of additional illustrations of embodiments clearly related to and based on this novel art, should not be construed as suggesting that they are not a part of the novel art of this invention.

This invention provides a Complete Fluid Exchange for Automatic Transmissions consisting of: 1—The utilization and coordination of a static fluid change which includes flushing, purging, cleaning of the pan and the cooling return line and its downstream circuits; and 2—A dynamic fluid exchange which includes the flushing, purging, cleaning of the remaining inaccessible components such as the torque convertor and other internal components which are only accessible with the use of this type of apparatus with the transmission operating.

This invention institutes this Complete Fluid Exchange in as short a period of time as feasible with the least amount of fluid utilized that is practical.

This invention provides the means to unequivocally replace the used fluid extracted during both the static and dynamic phases of the Complete Fluid Exchange in a coordinated, systematically controlled manner.

This invention provides the coordinated means to refill an automatic transmission in as short a time as feasible using the minimum amount of fresh fluid practical without creating any fluid starvation or other potentially harmful conditions in the transmission or vehicle during the dynamic part of the Complete Fluid Exchange.

Because the Complete Fluid Exchange System utilizes enigmatic, unobvious and novel art to attain these utilitarian and commercially useful results, it is therefore distinctly patentable. Each of the two embodiments of the invention specified in FIGS. 2 and 3 incorporate the use of a unique Pan Access Tube, which serves as a used fluid extraction means in both embodiments during the static phase of the Complete Fluid Exchange. It also serves with a second, dual use as an additional, coordinated means of fresh fluid introduction at a second locus during the dynamic phase of the Complete Fluid Exchange in the second preferred embodiment.

The invention provides an apparatus comprised of but not limited to: a source of fresh fluid and means to apply pressure to introduce that fresh fluid into the transmission at more than one locus; a reservoir to receive used fluid extracted from the transmission at more than one locus; a means to apply low pressure to these extraction loci such that used fluid is extracted from them; a means to measure and balance the flow rate and volume of fresh fluid introduced into the transmission and during the dynamic part of the fluid exchange the flow rate and volume of used fluid extracted from the transmission such that fresh fluid is simultaneously exchanged with used fluid at the same approximate rate without causing any starvation conditions or other potentially harmful conditions in any internal transmission component during the dynamic part of the Complete Fluid Exchange when the transmission is running, or during the static part of the Complete Fluid Exchange before the dynamic part of the exchange is instituted.

In summary, the invention has the capability to institute a Complete Exchange of fresh fluid for used fluid in the shortest time practical using the minimum amount of fresh fluid. It also has the capability of maintaining a balanced rate of flow between the fresh fluid being introduced and the used fluid being extracted. It has the capability to institute virtually a complete flushing and purging of used fluid with an essentially complete cleaning of the transmission. It also provides the operator with an easy to operate apparatus which can be used conveniently to attain the desired results which the Complete Fluid Exchange offers. These novel contributions to the art of changing fluid in automatic transmissions make the invention commercially useful and patentable.

Further objects and advantages of my invention will become apparent from a consideration of the drawings and ensuing description of each.

Figure 1:
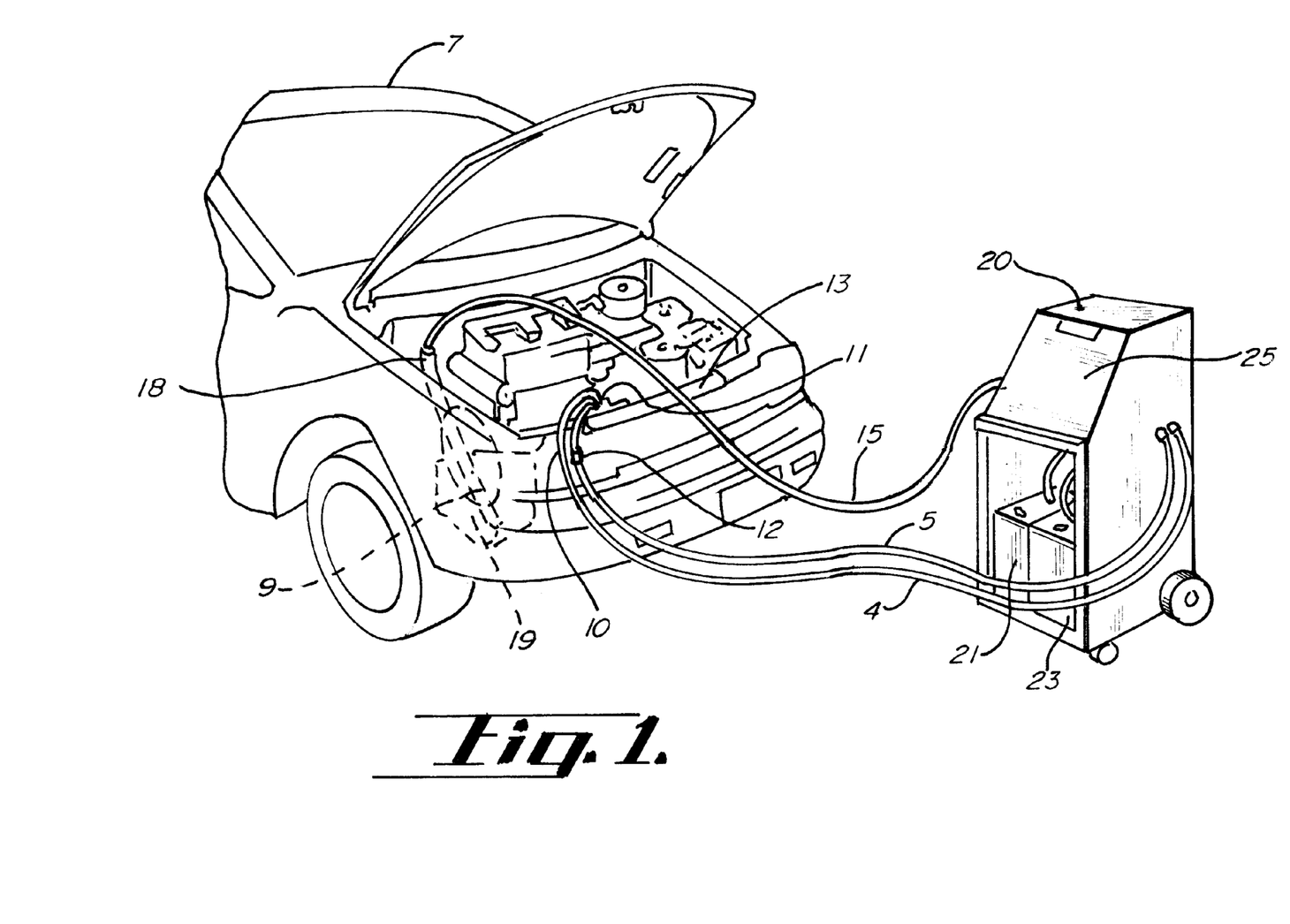
FIG. 1 is a representative illustration of the applicant's system as it is typically positioned with respect to a vehicle being serviced.

Description of the Complete Fluid Exchange System in Position—FIG. 1

FIG. 1 is a representative illustration of a Complete Fluid Exchange System 20 as it is typically positioned with respect to a vehicle being serviced. Complete Fluid Exchange System 20 is interconnected via a pair of interchangeable input/output hoses (an input/output hose 4 and an input/output hose 5) to a vehicle 7 being serviced which has an automatic transmission 9.

Hoses 4 & 5 are connected to either side opened cooling circuit (not shown) of vehicle 7 which connects to and runs through a transmission cooler 11 which is an integral part of a radiator 13. This is done by making random connection to a pair of quick connect stems (a quick connect stem 10 and a quick connect stem 12) which have been interconnected to the cooling circuit. A Pan Access Tube 15 has been inserted down into a transmission pan 19 via a transmission dipstick/filler tube 18. A used fluid receptacle 21 is used to receive the used fluid extracted from transmission 9 by the Complete Total Fluid Exchanger 20. A fresh fluid receptacle 23 is used to supply the fresh fluid which the Invention will introduce into transmission 9. Receptacle 23 is also used to supply the fresh fluid to pan 19 from a Pan Access Tube 15 in the second embodiment illustrated in FIG. 3. A control panel 25 is located on the front top of The Complete Fluid Exchange System.

Figure 2:
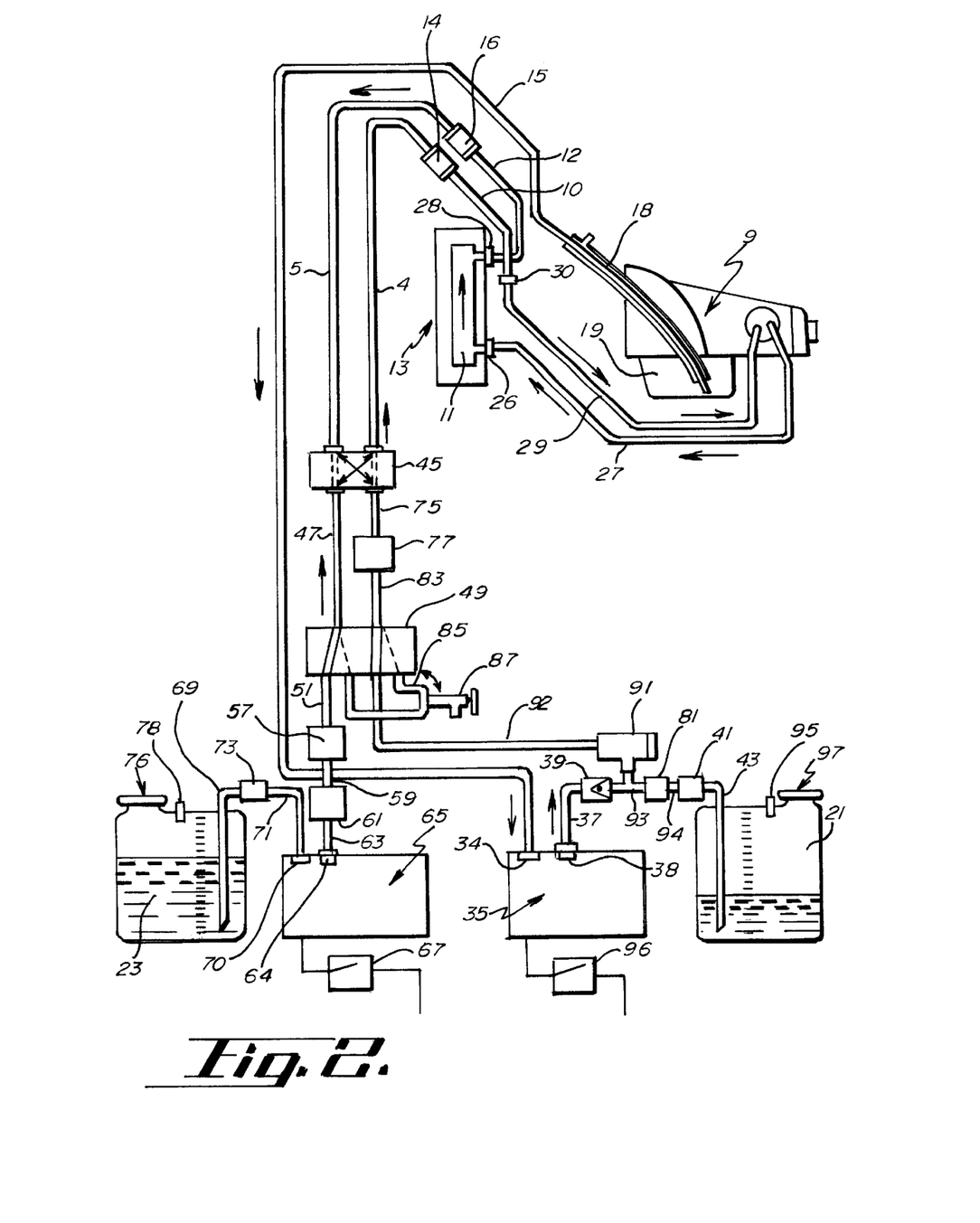
FIG. 2 is a schematic illustration of the first and most basic embodiment interconnected to a vehicular automatic transmission to be serviced by the invention.

Description of the Complete Fluid Exchange System—FIG. 2—The First Embodiment

FIG. 2 is an illustration of the first embodiment of the The Complete Fluid Exchange System which is randomly interconnected to both sides of an opened fluid cooling circuit 27/11/29, designated as 27/11/29 because before being opened it is comprised of a cooling outlet line 27, a transmission fluid cooler 11 inside a radiator 13 and a cooling return line 29, each of which form together a connected, complete cooling circuit of transmission 9. Input/output hoses 4 & 5 are shown interconnected to both sides of cooling circuit 27/11/29. Hose 4 is connected to line 29 at connector 30, through stem 10 which is connected to hose 4 by quick connector 14. Stem 10 is connected to the end of line 29 at connector 30 after connector 30 has been disconnected from a port 28 of cooler 11 (as an alternative choice, a port 26 of cooler 11 can be disconnected for the interconnection location if preferred by the operator). Hose 5 is connected to line 27 through stem 12 which is connected to hose 5 by quick connector 16 which is connected to opened port 28 of cooler 11, thereby connecting hose 5 to a transmission cooler 11 located in radiator 13.

Input/output hoses 4 & 5 are connected to two different ports, one each, of a flow alignment valve 45.

One end of Pan Access Tube 15 is connected to an auxiliary pump suction port 34 of an auxiliary pump assembly 35 with the other end of tube 15 inserted down dipstick/filler tube 18 into and down to the bottom of pan 19. Auxiliary pump 35 can be activated by an electric power supply switch 96, and when activated pump 35 delivers low pressure to Pan Access Tube 15, causing used fluid to flow through tube 15 to enter suction port 34 and to be pumped out of an outlet port 38 of pump 35 into an outlet line 37 of pump 35. Outlet line 37 is connected to outlet port 38 at one end and connected to a check valve 39 at the other end. A three port used fluid delivery line 93 connects check valve 39 to a fluid clarity sensor 81 and to the downstream side of an adjustable relief valve 91.

A used fluid delivery line 94 connects clarity sensor 81 to a quick connector 41 which connects line 94 to a used fluid delivery line 43 which carries the used fluid extracted from the transmission into used fluid receptacle 21.

Used fluid receptacle 21 has an opening with a closure 97 and a vent tube 95. Receptacle 21 has volume level indicating marks numbered in quarts (not shown). Input/output lines 4 & 5 are connected to flow alignment valve 45 which is shown in simple terms but can exist in many different forms without departing from the basic principle or art.

A used fluid delivery line 92 connects one port of a main on-off valve 49 to an adjustable relief valve 91. (Main valve 49 is a combination, multi-port, two-position flow direction selector valve-ports are not shown numbered specifically.) A fluid delivery line 47 is connects one port of main valve 49 to one port of flow alignment valve 45. Fresh fluid receptacle 23 is connected to a suction tube 69 which is in turn connected by a quick connector 73 to a fresh fluid suction line 71 which is connected to a suction port 70 of a main pump 65. An opening with closure 76 and a vent tube 78 is provided to fresh fluid receptacle 23. Receptacle 23 has volume indicating marks present similar to used fluid receptacle 21, but reversed to illustrate quarts of used fluid deposited (marks not shown).

Main pump 65 can be activated by an electric power supply switch 67, and when activated pumps fresh fluid through an outlet port 64, into a fresh fluid delivery line 63 and through adjustable flow regulator 61. A fresh fluid delivery line 59 connects regulator 61 to a combination rate of flow and total volume of flow indicator/meter which indicates rate of flow and volume of fresh flow delivered, a fresh fluid flow rate/totalizer meter 57. Fresh fluid delivery line 51 connects meter 57 to main valve 49. A fluid delivery line 47 connects one port of main valve 49 to one port of flow alignment valve 45.

A used fluid delivery line 83 connects one port of main valve 49 to a bidirectional combination indicator/meter which indicates direction of used flow, rate of used flow, and total volume of used flow, a used flow rate/totalizer meter 77. A used fluid delivery line 75 connects meter 77 to one port of flow alignment valve 45. A three port used fluid bypass line 85 connects two ports of main valve 49 with a sample tap 87.

Description of Operation of the First Embodiment of FIG. 2

To initiate the use of the invention, used fluid receptacle 21 is emptied through an opening with closure 97 after disconnecting connector 41 and then reconnected to connector 41 so that an empty receptacle is available to receive the used fluid extracted from the transmission 9 being serviced. Fresh fluid receptacle 23 is filled through an opening in closure 76 while in place, but receptacle 23 can be removed by disconnecting it at connector 73 to fill it, and then replacing it in position in the Complete Fluid Exchanger System 20 (FIG. 1) and reconnecting connector 73. In heavy duty or fleet applications, it is commercially useful to connect the invention to receptacles much larger than receptacles 21 & 23, but because the operating principles remain the same, it should be considered an extension of this same art and practice.

The cooling circuit 27/11/29 is opened at port 28 where line 29 is connected to cooler 11. The operator's selection of the location to open cooling circuit 27/11/29 at port 28 is random and made at the preference of the operator as a matter of ease and convenience. There are a number of other areas circuit 27/11/29 is suitable for opening, including connection 26.

Stem 12 is connected to the outlet side of the opened cooling circuit, outlet line 27 by connecting it to port 28 of cooler 11 and stem 10 is connected to the inlet side of the opened cooling circuit by connecting it to connector 30 of cooling return line 29. The invention's input/output hoses 4 & 5 are randomly connected to the opened cooling circuit 27/11/29, but in this illustration for sake of example input/output hose 4 is connected to cooling return line 29 through stem 10, and input/output hose 5 is connected to cooling outlet line 27 thought cooler 11 and stem 12. Pan Access Tube 15 has been inserted directly into the bottom of pan 19 by pushing it down dipstick/filler tube 18.

The invention is now ready to be operated. The vehicle is started and run with the transmission in park and the fluid level of pan 19 is checked and corrected if out of the range desired. The used fluid contained in transmission 9 is now circulating through cooling line 27 into hose 5 through stem 6 which is connected to hose 5 by quick connector 16 and into the invention, through the invention, and out of the Complete Fluid Exchanger 20 (FIG. 1) and back through hose 4 and into the cooling return line 29 as the Complete Fluid Exchanger 20 (FIG. 1) functions in an Off/bypass mode with the transmission operating in park (indicated with dotted lines at main valve 49). The used fluid flows from line 27 to hose 5 to flow alignment valve 45, through valve 45 into line 75 to used meter 77.

The used fluid from hose 5 then flows from meter 77 through line 83 to main valve 49, through main valve 49 and into bypass line 85 and back through valve 49 to line 47, through line 47 to alignment valve 45, through alignment valve 45 to input/output hose 4, and through quick connector 14, through stem 10 and into cooling return line 29 which carries the used fluid back into transmission 9.

Flow alignment valve 45 is controlled in response to the direction of flow indicated at meter 77. Flow alignment valve 45 is a two position flow direction selector valve which switches direction of flow between lines connecting valve 45 and main valve 49, thus providing the capability to randomly connect the input/outlet hoses 4 & 5 to either side of opened cooling circuit 27/11/29. Alignment valve 45 permits quick alignment of the direction of flow in cooling circuit 27/11/29 with the direction of flow in the two main subsystems, the used fluid extraction system and the fresh fluid introduction system which are contained in the Complete Fluid Exchange System. In the embodiment illustrated in FIG. 2 valves 45 & 49 and used flow meter 77 are mechanically operated and can also be electrically operated, microprocessor controlled, and electronically indicating. While very sophisticated electronic microprocessor combinations can be used to make the contents of the invention more compact, they certainly retain the same principles or art utilized in FIG. 2 and should not be considered significant variants of the novel art presented herein.

Also, valves 45 & 49 as depicted in FIG. 2 are illustrated in most basic form for simplicity of illustration. Various other more dispersed variants comprised of multiple solenoid or manually operated subunits can be utilized which operate under the same principle of art when examined in unity, but do not vary from the actual scope of what is illustrated in this embodiment.

If the used fluid is flowing through cooling circuit 27/11/29 such that when randomly connected to the invention with valve 49 in its Off/bypass mode (dotted line) meter 77 indicates that the flow is not in alignment with the invention, then flow alignment valve 45 is actuated to its second, alternate position which institutes a flow alignment condition which is clearly indicated at meter 77.

Meter 77 then indicates proper flow alignment, and also indicates the rate of flow at which the used fluid is being circulated through cooling circuit 27/11/29 as bypassed through closed loop 85 and the operator makes note of this.

Because main valve 49 is in its Off/bypass position (dotted lines), the used fluid passes only through the valve ports connected to both sides of bypass line 85. The operator then uses sample tap 87 to draw a sample of the used fluid circulating in the cooling circuit into a clear sample vial to later give to the vehicle's owner.

The engine is then turned off which inactivates transmission 9 placing it in a static mode. Electrical supply switch 96 is then activated by the operator which activates auxiliary pump 35 which applies low pressure to the used fluid in pan 19 via tube 15. Tube 15 is a clear hose which allows the operator to visually monitor the presence and approximate clarity (estimated degree of non-contamination) of the used fluid which then is forced by air pressure into line 15, through pump 35 and then deposited in used receptacle 21.

The actual clarity of the used fluid being extracted is indicated by clarity indicator 81, which in a microprocessor operated embodiment, provides electronic indicating signals to the microprocessor.

When the operator notices that the used fluid from pan 19 passing through tube 15 runs out and only air is being pushed through the line by atmospheric air pressure, suggesting the pan is near empty or empty, the operator activates electrical supply switch 67 which activates main pump 65 which applies low pressure to the fresh fluid contained in tank 23 through lines 71 & 69. This causes the fresh fluid to move into inlet port 70 of pump 65 where pressure is applied to force it into line 63 and all other lines down line from line 63 which will be connected to it when main valve 49 is activated.

The operator then moves main valve 49 to in secondary or On position (solid line) which allows the fresh fluid forced into line 63 by pump 65 to flow through flow regulator 61 through line 59 to flow meter 57, through line 51 to the main valve 49 to line 47, through line 47 to alignment valve 45, through alignment valve 45 and to input/output hose 4 and then into the return cooling line 29. As the fresh fluid now flows through the fresh fluid introduction subsystem of the invention and into the return side of the opened cooling circuit, it then flows to the internal transmission components downstream to the return side of the cooling circuit and eventually comes to rest in pan 19. As this fresh fluid so flows, the operator adjusts flow regulator 61 such that the rate of flow of fresh fluid approximately matches the rate at which used fluid was measured at meter 77 to have been circulating at in the cooling circuit when the invention was in bypass mode with the transmission operating in park. After so operating the invention for a brief period, the operator notices that fluid begins to flow once again through tube 15 and later begins to show clarity in tube 15 and at used clarity sensor 81, suggesting that the return cooling line and its downstream components and circuits have been flushed and purged into pan 9. As the fluid now moving through tube 15 reaches clarity, the operator inactivates main valve 49 by moving its selector to the alternate Off/bypass position, which leaves pump 65 on, but not delivering fresh fluid into transmission 9 because main valve 49 now has closed fresh fluid delivery line 51 (this will not harm the pump because it has an internal relief/unloader system designed to protect it during these times of running and not delivering fresh fluid into transmission 9).

The operator then examines the volume indicating marks of both receptacles 21 & 23 (not shown specifically) and subtracts the approximate volume of fresh fluid delivered from the used fluid received to calculate the approximate volume of additional fresh fluid that must now be pumped into pan 19 through the cooling return line 29 in order to fill it to its normal operating level so the dynamic part of the Complete Fluid Exchange can be instituted. The operator again activates valve 49 (with the transmission still not operating) and continues adding fresh fluid to pan 19 through cooling return line 29 until the additional calculated amount has been introduced into the pan as indicated on fresh receptacle 23 by its volume indicating marks. Main valve 49 is now moved to its Off/bypass mode position once again.

The static part of the Complete Fluid Exchange has been completed. The return cooling line 27 and its downstream circuits and components including pan 19 have been flushed, purged, cleaned and then refilled and left holding fresh fluid. Pan 19 is now filled with the proper amount of fresh fluid. Now the operator is ready to institute the dynamic part of the Complete Fluid Exchange.

The vehicle is now started and idled with the transmission 9 placed in park and main valve 49 is simultaneously activated by moving it to its On position which begins the dynamic part of the Complete Fluid Exchange in which fresh fluid is pumped from receptacle 23 into return cooling line 29 and used fluid is extracted out of cooling outlet line 27 from the transmission components which were not already flushed, purged, cleaned and refilled during the static part of the Complete Fluid Exchange.

As main valve 49 is activated, adjustable relief valve 91 is quickly calibrated to cause the rate of flow of used fluid to approximate the rate of flow of fresh fluid as indicated at fresh flow indicator 77, and an approximate balance between the rate at which fresh fluid flows into transmission 9 at and the rate that used fluid flows out of transmission 9 at now occurs. That is, fresh fluid is now being introduced into cooling return line 29 at essentially the same approximate rate that used fluid is being extracted from cooling outlet line 27.

The Complete Fluid Exchange is continued at this essentially balanced rate of fluid exchange until clarity sensor 81 indicates that the fluid being extracted from cooling outlet line 27 is now substantially as clean as fresh fluid which confirms that essentially all of the fluid circulating in the transmission is fresh now. This also indicates that the transmission has been completely flushed, purged, cleaned and refilled with fresh fluid.

When the desired clarity of the fluid being extracted from cooling outlet line 27 is attained as indicated by sensor 81, the main valve is inactivated, again placing the invention in its Off/bypass mode and the final fluid sample is taken at tap 87 by the operator who will give it and the first sample to the vehicle owner or customer.

The Complete Fluid Exchange System 20 (FIG. 1) is now turned off (even when off it will still allow the transmission's fluid to pass through its input/output hoses 4 & 5 in either direction, unobstructed). Then the vehicle is turned off as well.

The operator can examine the volume indicating marks on fresh receptacle 23 which will indicate just how much fresh fluid was used for purposes of billing the vehicle's owner and for maintaining inventory control of fresh fluid supplies.

Input/output hoses 4 & 5 are now disconnected at quick connectors 14 & 16. Stems 10 & 12 are then disconnected from both sides of the opened cooling circuit at port 28 and connection 30. Cooling return line 29 is then reconnected to port 28 at connection 30 to close the previously opened cooling system 27/11/29.

The vehicle is now started with the transmission in park and the operator checks the cooling circuit for any leaks should the connections not be secure. The operator then checks the fluid level of the transmission by use of the dipstick (not shown) inserted in dipstick/filler tube 18. The Complete Fluid Exchange as instituted by use of the first embodiment as illustrated in FIG. 2 is now finished.

Figure 3:
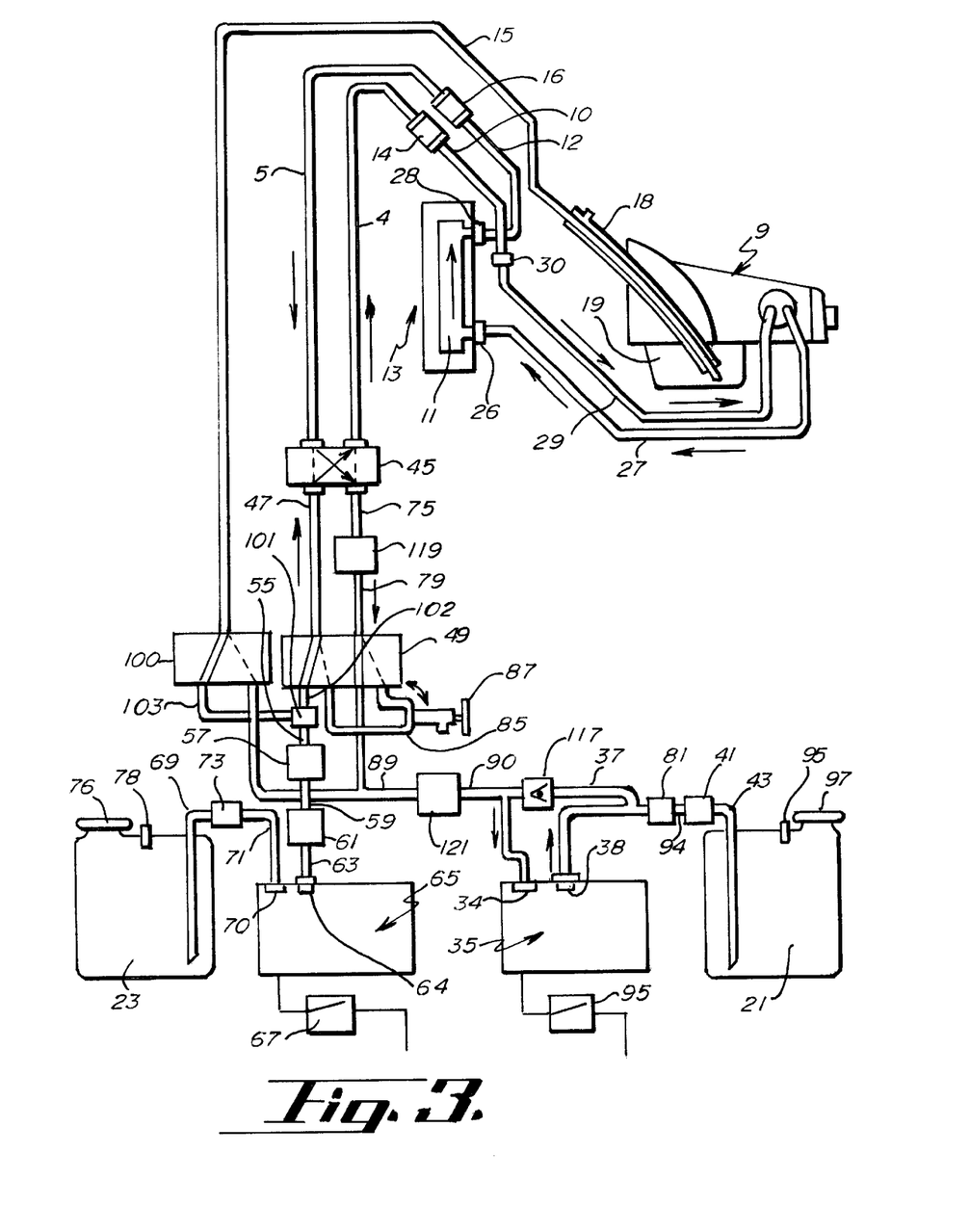
FIG. 3 is a schematic illustration of the second, preferred embodiment interconnected and positioned to a vehicular automatic transmission to be serviced by the invention.

Description of the Invention—FIG.3—the Second Embodiment

FIG. 3 is an illustration of the second and preferred embodiment of the Invention, the Complete Fluid Exchange System which like the embodiment illustrated in FIG. 2, has been randomly interconnected to both sides of the opened cooling circuit comprised of cooling outlet line 27, transmission 11 inside radiator 13 and cooling return line 29, each of which form together as connected, the complete cooling circuit 27/11/29 of transmission 9. Both embodiments share most of the integral components and/or means utilized. The second and preferred embodiment is electrically powered and electronically controlled by a microprocessor system provided with suitable software. The microprocessor receives electronic indicating signals from electronically indicating sensors and meters, processes them according to the software specifications and then elicits electronic command signals to individual components which are electronically controlled and electrically powered. The specific wiring harness, microprocessor parts, circuits and connectors are not included in FIG. 3 for sake of brevity and because they are quite basic to their art. Lack of specific inclusion of all microcircuit diagrams, which are microscopic, and lack of inclusion of all wiring, connection and power supply specifics should not be construed to limit the scope of the novel art inclusive to this embodiment.

Input/output lines 4 & 5 are shown interconnected to both sides of the cooling circuit comprised of 27 & 29 with line 4 connected to line 29 via stem 10 which is connected to the end of line 29 which was disconnected from port 28. Line 5 is connected to line 27 via stem 12 which is connected opened port 28 which also at the same time connects line 5 to a cooler 11 located in radiator 13. One end of Pan Access Tube 15 is connected to the one port of an auxiliary three way valve 100 and the other end of tube 15 has been inserted down dipstick/filler tube 18 and to the bottom of pan 19.

A three port used fluid delivery line 89 connects a combination used fluid flow rate/totalizer meter 121 to one port of main valve 49 and to one port of the auxiliary valve 100. A three port used fluid delivery line 90 connects meter 121 to a check valve 117 and to port 34 of auxiliary pump 35. Pump 35 has an outlet port 38 which is connected to a three port used fluid delivery line 37 which connects port 38 to check valve 117 and to a fluid clarity sensor 81. A used fluid delivery line 94 connects clarity sensor 81 to connector 41 which is connected to a used fluid delivery line 43 which extends into a used reservoir 21. Used reservoir 21 is provided with opening with closure 97 and vent tube 95. A used fluid delivery line 75 connects flow alignment valve 45 to a combination flow direction, rate of flow meter 119 which is connected to main valve 49 by a used fluid delivery line 79.

Input/output hoses 4 & 5 are connected to a flow alignment valve 45 which is shown in simple terms but can exist in many different forms or combinations without departing from the basic principle or art. There are many different ways to organize smaller solenoid valves and similar means to attain the same principles of novel art contained in this embodiment and it should be assumed that it is not necessary to list every single alternative possible to define the spirit and method of such novel art.

A fluid delivery line 47 is connected to one port of flow alignment valve 45 at one end and to one port of main valve 49 which serves as a combination, two position, on/off valve with two modes of operation. One mode results when main valve 49 is in the Off/bypass position (dotted lines) where lines 47 and 79 are connected together by a used fluid bypass line 85 which is also connected to sample tap 87. The second mode results when main valve 49 is in the On position (solid lines) where line 47 is connected to line 102 and line 79 is connected to a 3 ported used fluid delivery line 89.

Main valve 49 is shown in simple terms but can exist in many different much more sophisticated, complex forms without departing from the basic principle or art. The ports are not numbered for sake of simplicity and due to common understanding of one knowledgeable in the art.

Fresh fluid receptacle 23 is connected by suction tube 69 which is in turn connected by connector 73 to fresh fluid suction tube 71 which transports fresh fluid into the inlet port 70 of main fresh fluid pump 65. Opening with closure 76 and vent tube 78 is provided to fresh fluid receptacle 23. Main pump 65 is electrically powered by a source energized by switch 67. Outlet port 64 of pump 65 is connected to adjustable flow regulator 61 by a fresh fluid output delivery line 63. A fresh fluid delivery line 59 connects adjustable flow regulator 61 to fresh fluid flow rate/totalizer meter 57. Fresh flow meter 57 is connected by fresh fluid delivery line 55 to a fluid proportioning valve 101, which is comprised in this case of an adjustable relief valve which has two ports. One port, the regulated port, is connected by a fresh fluid delivery line 102 to one port of main valve 49. The other port, the relieved port, is connected by a fresh fluid delivery line 103 to a port on auxiliary valve 100.

Each of these valves is connected via a wiring harness to a microprocessor system which receives electronic indicator signals, and processes them according to the suitable software design installed in the microprocessor assembly. The microprocessor assembly, after processing indicator signals according to the software design, then elicits electronic command signals to appropriate valves and controls which are electronically activated and electrically powered. In this manner, then, many of the invention's operations are instituted.

It should be understood that if all of these valves and indicators were strictly mechanical and manually operated instead of electrically powered, electronically controlled and operated as described in this embodiment, there would be no significant difference in scope or function from the principles of novel art utilized in this invention.

It should also be understood that there are many different ways to pump fluid, that is, there are many different suitable ways to apply pressure to fluid for purposes of forcing it through a line and a number of ways to apply low pressure to the fluid in a line such that atmospheric or air pressure will force it through that line in the direction of the low pressure as intended. Pumping systems can be powered by gravity, heat, electricity, fuel operated motors, and other means. The actual means used to apply pressure or low pressure to the fluid is not important, but it is the principle of the art which is important as expressed in the overall function of the pumping system and what it can attain. It should not be construed that by not listing all possible specific pumping possibilities by including numerous additional embodiments with minor changes to illustrate them, that the scope of the art illustrated in this embodiment is in any way limited by such constraint which was exercised for sake of brevity.

All possible design layouts and similar combinations within the scope of this novel art have not been included for the sake of brevity. Minor changes in layout which do not significantly depart from the spirit of this art should not be construed to be significantly divergent.

Description of Operation of the Second Embodiment Illustrated in FIG. 3

To initiate the use of the invention, used fluid receptacle 21 is emptied through tank access cap 97 after disconnecting connector 41 and then reconnected to connector 41 so that an empty receptacle is available to receive the used fluid extracted from the automatic transmission being serviced. Fresh fluid receptacle 23 has been filled through tank access cap 76 with the tank in place, but tank 23 could have been removed by disconnecting it at quick connector 73, filling it and then returning it into position in the invention 1 (FIG. 1) and reconnecting connector 73.

In heavy duty or fleet applications, the invention is hooked up to much larger tanks in lieu of receptacles 21 & 23 respectively which do not require emptying at each service operation, but only periodically after a substantial number of services depending on the size of the receptacles. Since the operating principles remain the same, such minor modifications should be considered an extension of this same art and practice.

Lines 27 & 29 which connected to a cooler 11 located in the vehicle's radiator 13 comprise the cooling circuit and are designated as 27/11/29. Cooling circuit 27/11/29 is opened at a cooler port 28 by disconnecting cooling line 29 where line 29 is connected to cooler 11. The selection of where to open the cooling circuit 27/11/29 is made at the preference of the operator as a matter of ease and convenience. There are a number of other areas circuit 27/11/29 could be opened including connection 26.

Stem 10 is connected to the outlet side of the opened cooling circuit 27 at connector 30 of line 29. Stem 12 is connected to port 28 on 11. The invention's input/output hoses 4 & 5 are randomly connected to the opened cooling circuit 27/11/29, but in this illustration for sake of example are shown as input/output hose 4 connected to cooling line 29 through stem 10, and input/output hose 5 connected to cooling outlet line 27 through cooler 11 and stem 12. Pan access tube 15 has been inserted directly down into the bottom of pan 19 by pushing it down dipstick/filler tube 18.

The invention is now ready to be operated. The vehicle is started and run with the transmission in park and the fluid level of pan 19 is checked. If it is not at the normal operating level that is corrected. The invention is turned on by activating an on/off power switch on the control panel which is not shown for sake of brevity.

The used fluid contained in transmission 9 is now circulated through cooling outlet line 27 into hose 5 into, through and then out of the Complete Fluid Exchanger System 20 (FIG. 1) and back through hose 4 and into the cooling return line 29 as the invention functions in an Off/bypass mode due to the position that main valve 49 is in (as indicated by the dotted lines).

The used fluid flows from hose 5 through flow alignment valve 45 into line 75 which delivers it to meter 119 which indicates that the used fluid is flowing in the correct direction, and that the invention is in proper alignment with the direction of flow in the cooling circuit. Meter 119 also indicates the rate at which the used fluid is flowing through the cooling circuit which has been reclosed by line 85 in combination with main valve 49 being in its Off/bypass mode. The used fluid now flows from meter 119 through line 79 to one port of main valve 49, through used fluid bypass line 85, back through main valve 49 and out of valve 49 through line 47 to alignment valve 45 and into line 4 and finally through cooling return line 29.

If the direction of flow in the cooling circuit was reversed and not flowing in alignment with the Complete Fluid Exchange System 20 (FIG. 1) it would still flow through a closed loop bypass which flows in and out of main valve 49 through bypass line 85, but meter 119 would indicate a non-alignment condition which would automatically signal the microprocessor which would then trigger a signal to an electric solenoid to move alignment valve 45 to its alternate position, thus establishing alignment between the direction of flow in the cooling circuit of the vehicle being serviced and the direction of flow within the invention as indicated at meter 119. The direction of flow of the used fluid through this closed loop) is established by how each one of hoses 4 and 5 were selected to attach to each one of the stems 10 or 12. The invention allows for speedy random choice in making this connection by the operator, an important commercial consideration. FIG. 3 illustrates correct alignment for sake of illustration with solid lines at valve 45.

The used fluid from the cooling outlet line 27 is now flowing through the invention in the correct direction through bypass line 85 and back into cooling return line 29. The operator now of fluid before the Complete Fluid Exchange is instituted and will be given to the vehicle owner or customer along with the second sample that is drawn after all of the fluid of Transmission 9 has been changed by the Complete fluid Exchange System 20 (FIG. 1).

Now that the sample is taken, the engine is then turned off which inactivates transmission 9 placing it in a static mode. The operator activates an electrical supply switch mounted on a control panel 25 (see FIG. 1 for the location of the control panel, details not shown) which activates the microprocessor which in turn closed the power supply switch 95 thereby activating the auxiliary pump 35 which applies low pressure to the used fluid in pan 19 via tube 15 through auxiliary Valve 100 which is at rest in its off position (dotted line).

This application of low pressure into and through tube 15 results in the fluid contained in pan 19 moving up into tube 15 and through valve 100, through line 89 through meter 121 through auxiliary pump 35 and out of pump 35 through line 37, through clarity sensor 81 and through line 43 and into the used reservoir 21. When clarity sensor 81 indicates a lack of fluid clarity, the microprocessor activates fresh fluid supply pump 65 by closing electric supply switch 67 and activates main valve 49 placing it in its On position (indicated by solid lines).

The activation of pump 65 with valve 49 results in fresh fluid being forced from port 64 of pump 35 through line 63 through adjustable flow regulator 61, through line 59 through meter 57, through line 55 to adjustable relief valve 101 (used as a proportioning valve set to minimum line pressure necessary to prevent starvation in line 29) and into line 102, through main valve 49 to line 47, through alignment valve 45, to hose 4 which carries the fresh fluid into the cooling return line. This fresh fluid flushes, purges, cleans and refills those down line transmission components while simultaneously depositing the diluted, mixture of clean and used fluid in the pan 19 (FIG. 1) where it is forced out by atmospheric air pressure through tube 15 and into receptacle 21, while pump 35 is still running and connected to tube 15. Proportioning valve 101 is a spring loaded relief type valve which is set to keep a minimum pressure on the return cooling line 29 in the range of 10–15 PSI, such that there will not be any fluid starvation type conditions, or overpressurization down-line which could damage downstream transmission components. This valve is set such that the majority of the fresh fluid being introduced into transmission 9 will be through Pan Access Tube 15 for most vehicles.

The mixed, diluted fluid from the down line components of the cooling return line 29 is deposited and removed by tube 15 as it is deposited in pan 19 (FIG. 1) with increasing clarity as time passes. As soon as clarity sensor 81 indicates that the fluid being extracted through tube 15 is essentially as clean as fresh fluid, the microprocessor sends a command signal to turn off main valve 49 and another signal to turn on the auxiliary valve 100 (solid line) such that it allows fresh fluid to be pumped into the pan directly through tube 15 from pump 65 until the pan has been filled. This amount has been calculated by the microprocessor based on previous signal input from meter 121, which has indicated how much fluid was extracted so far.

The microprocessor will move switch 67 to its Off position when it receives a signal from fresh fluid totalizer meter 57 that the same amount of fluid has been pumped out of fresh fluid reservoir 23 that has been received in used fluid reservoir 21 as indicated by meter 121. This result will cause a toned/lighted signal to be given off by the microprocessor through an indicator mounted on control panel 25 (FIG. 1, not specifically shown) to signal the operator that the static part of the Complete Fluid Exchange is now complete and both pumps 65 & 35 are deactivated. Now the operator is ready to institute the dynamic part of the Complete Fluid Exchange.

The vehicle is started and run with the transmission in park. Meter 119 indicates to the microprocessor that used fluid is flowing out of the cooling outlet line into used fluid bypass line 85 and this causes the microprocessor to send command signals which simultaneously activate both pumps 65 & 35, and at the same time move main valve 49 to its On position (solid line) and also move auxiliary valve 100 to its On position (solid line). This combination of signals cause fresh fluid to be pumped through hose 4 into the return cooling line 29 and through tube 15 directly into the transmission pan, both simultaneously.

At the same time fresh fluid is being pumped into the transmission at two different entry points (pan 19 and return cooling line 29), auxiliary pump 35 is applying low pressure to line 37 which increases the flow of used fluid out of the transmission through cooling outlet line 27, especially in low flow situations occasionally encountered with small foreign type designed transmissions. This used fluid which is being pumped out of transmission 9 through cooling outlet line 27, ending up in used reservoir 21, is pumped out by force applied by transmission 9's own internal pump, added to the low pressure applied from pump 35.

The rate at which used fluid is being extracted from the cooling outlet line 27 and into used receptacle 21 is measured by meter 121. The overall sum/total rate at which fresh fluid is being pumped into the transmission through lines 15 and 29 is indicated by meter 57. This rate is kept closely matched to the rate of used fluid extraction as indicated by meter 121.

The balance maintained between the total amount of fresh fluid introduced into the transmission (from both loci, Pan Access Tube 15 and hose 4) with the total amount of used fluid extracted is based on the microprocessor's comparative processing of indicating signals from meter 121 and meter 57. The microprocessors command signals to adjustable flow regulator 61 places total fresh fluid flow at the desired levels during the dynamic part of the Complete Fluid Exchange.

This process of introducing fresh fluid at two different loci into transmission 9 at an overall rate which is balanced to the rate at which used fluid is being extracted continues until clarity sensor 81 indicates that the used fluid being extracted has the same essential clarity as fresh fluid.

At this point the microprocessor sends command signals to deactivate both pump 65 and pump 35 and to move main valve 49 back to its Off/bypass position. This allows the fluid to now once again circulate through bypass line 85. The operator now takes the final fluid sample from tap 87 which has the same clarity of the fluid circulating in the cooling circuit 27/11/29, which also has the same essential clarity as the last volume of fluid which passed through clarity sensor 81. The dynamic part of the Complete Fluid Exchange is now over and the vehicle's engine is stopped.

Hoses 4 & 5 are now disconnected at connectors 14 & 16. Stems 10 & 12 are then disconnected from both sides of the opened cooling circuit at port 28 and connector 30. Cooling return line 29 is then reconnected to port 28 at connector 30 to reclose the opened cooling system 27/11/29.

The vehicle is now started with the transmission in park and the operator checks the cooling circuit for any leaks should the connections not be secure. The operator then checks the fluid level of the transmission by use of a dipstick (not shown) inserted in dipstick/filler tube 18.

The complete Fluid Exchange as instituted by use of the second embodiment as illustrated in FIG. 3 is now finished. The operator turns off the Invention and moves it out of position so that the vehicle can be moved. Periodically the microprocessor is downloaded to monitor fresh fluid usage for purposes of inventory control.

Summary, Ramifications and Scope of Invention

Thus the reader will see that the Complete Fluid Change System provides a unique, highly effective, convenient, compact, easy to operate, rapid and cost efficient device to institute a Complete Fluid Exchange in vehicular automatic transmissions.

The device allows the operator to provide Complete Fluid Exchanges to vehicular automatic transmissions faster and easier, using less fresh fluid in the process. It provides before and after fluid samples for vehicle owners. For these reasons mentioned, it is novel art that is commercially useful and valuable in the automotive and vehicular maintenance industry.

While my above description contains many specifics, these should not be construed as limitations on the scope of the invention, but rather as exemplification of two embodiments thereof. For example, there are many similar ways to illustrate certain of the device's valve and indicator functions as numerous single entity components organized in more complex fashion while functioning in the same overall manner as illustrated in my figures and described in my specifications. These variants should not be construed as significantly different from the novel art presented in my specifications or claims but should be considered as a part of this same novel art my device is based on. These many possible small changes and alternative methods to express the same principles of the novel art of my device are not important enough to illustrate in the drawings. Accordingly, the scope of the invention should be determined not by the embodiments illustrated, but by the appended claims and their legal equivalents.

Used fluid is extracted at only one locus during the static part of the invention's Complete Fluid Exchange, but in future related embodiments may be extracted from other loci simultaneously or in unison from additional loci or ports available on or in the transmission and should be considered direct use of this novel art.

Used fluid may also be extracted at more than one loci during the invention's dynamic part of the complete total fluid exchange in additional embodiments and should then be considered direct use of this novel art.

What is claimed is:

1. A fluid exchange system for use in exchanging a used fluid with a fresh fluid in a vehicle having an automatic transmission and a fluid cooling circuit operatively connected to conduct a circulated fluid therein, said transmission having a dipstick filler tube, said fresh fluid being contained in and dispensed from a source external to said vehicle, said used fluid initially being contained within said vehicle and discharged into a receptacle external to said vehicle, said fluid exchange system comprising:

a first fluid line fluidly coupling the fluid exchange system, the source, the fluid cooling circuit, and transmission dipstick filler tube to conduct fresh fluid from the source into both the fluid cooling circuit and the dipstick filler tube, said conducted fresh fluid having a first fluid flow rate;

a second fluid line interconnected to the fluid exchange system and the vehicle to conduct the used fluid from the vehicle, said used fluid having a second fluid flow rate; and a control assembly operatively coupled to the first fluid line or the second fluid line to substantially balance the first fluid flow rate with the second fluid flow rate during an exchange procedure.

2. The fluid exchange system of claim 1 wherein the second fluid line is interconnected to the fluid cooling circuit of the vehicle.

3. The fluid exchange system of claim 1 further comprising:

at least one fluid meter operatively coupled to the first fluid line or the second fluid line.

4. The fluid exchange system of claim 2 further comprising:

an alignment mechanism operatively connected to the fluid exchange system for aligning the flow of the fresh fluid relative to the flow of circulated fluid within the fluid cooling circuit.

5. The fluid exchange system of claim 1 wherein the fresh fluid is pressurized by a pump operatively coupled to the first fluid line.

6. The fluid exchange system of claim 1 wherein the fresh fluid is simultaneously conducted into both the fluid cooling circuit and the dipstick filler tube.

7. The fluid exchange system of claim 1 further comprising:

at least one quick coupling assembly for selectively interconnecting the fluid exchange system to the vehicle.

8. The fluid exchange system of claim 1 further comprising:

a used fluid pump operatively coupled to the second fluid line for assisting in an extraction of used fluid from the vehicle.

9. A fluid exchange system for use in exchanging a used fluid with a fresh fluid in a vehicle having an automatic transmission and a fluid cooling circuit operatively connected to conduct a circulated fluid therein, said transmission having a dipstick filler tube, said fresh fluid being contained in and dispensed from a source external to said vehicle, said used fluid initially being contained within said vehicle and discharged into a receptacle external to said vehicle, said fluid exchange system comprising:

a first fluid line fluidly coupling the fluid exchange system, the source, the fluid cooling circuit, and transmission dipstick filler tube to conduct fresh fluid from the source into both the fluid cooling circuit and the dipstick filler tube, said conducted fresh fluid having a first fluid volume;

a second fluid line interconnected to the fluid exchange system and the vehicle to conduct the used fluid from the vehicle, said used fluid having a second fluid volume; and a control assembly operatively coupled to the first fluid line or the second fluid line to substantially balance the first fluid volume with the second fluid volume upon completion of an exchange procedure.

10. A fluid exchange system for use in exchanging a used fluid with a fresh fluid in a vehicle having an automatic transmission and a fluid cooling circuit operatively connected to conduct a circulated fluid therein, said transmission having a dipstick filler tube, said fresh fluid being contained in and dispensed from a source external to said vehicle, said used fluid initially being contained within said vehicle and discharged into a receptacle external to said vehicle, said fluid exchange system comprising:

a fist fluid line intercoupled to the fluid exchange system, the source, and the fluid cooling circuit to conduct fresh fluid from the source into the fluid cooling circuit, said conducted fresh fluid having a first fluid flow rate;

a second fluid line intercoupled to the fluid exchange system, the fluid cooling circuit, and the dipstick filler tube to conduct used fluid from both the cooling circuit and the dipstick filler tube, said used fluid having a second fluid flow rate; and a control assembly operatively coupled to the first fluid line or the second fluid line to substantially balance the first fluid flow rate with the second fluid flow rate during an exchange procedure.

11. The fluid exchange system of claim 10 wherein the second fluid line is interconnected to the fluid exchange system, the fluid cooling circuit, and the dipstick filler tube to simultaneously conduct used fluid from both the cooling circuit and the dipstick filler tube.

12. The fluid exchange system of claim 11 further comprising:

at least one fluid meter operatively coupled to the first fluid line or the second fluid line.

13. The fluid exchange system of claim 10 further comprising:

an alignment mechanism operatively coupled to the fluid exchange system for aligning the flow of the fresh fluid relative to the flow of circulated fluid within the fluid cooling circuit.

14. The fluid exchange system of claim 10 further comprising:

a pump coupled to the second fluid line for assisting in an extraction of used fluid from both the dipstick filler tube and the fluid cooling circuit.

15. A method for exchanging a used fluid with a fresh fluid in a vehicle having a transmission connected to a fluid circuit for conducting a circulated fluid therein in an operational direction, said used fluid initially being contained within said transmission and said fluid circuit, at least a substantial portion of which is subsequently discharged into a receptacle, said fresh fluid initially being contained in a source container, said method comprising the steps of:

providing a fluid exchange system having a first conduit for communicating fresh fluid to the transmission and a second conduit for communicating used fluid from the transmission, said fluid exchange system having a selectively coupled bypass circuit between the first conduit and the second conduit, said fluid exchange system having a fluid flow alignment mechanism;

coupling the bypass circuit between the first conduit and the second conduit;

coupling said fluid exchange system to the fluid circuit of the vehicle such that the used fluid flows from the transmission through the first conduit, the second conduit, and the bypass circuit and is returned to the transmission;

operating said fluid flow alignment mechanism to align the flow of the used fluid relative to the exchange system;

uncoupling the bypass circuit between the first conduit and the second conduit; and pumping a quantity of the fresh fluid through the first conduit sufficient to substantially replace the used fluid within the transmission and the fluid circuit from the source container into the transmission and the fluid circuit within the vehicle as the used fluid is expelled from the transmission and the fluid circuit through the second conduit and into the receptacle at substantially equivalent volumetric flow rates.

16. The method of claim 15 wherein the step of pumping is accomplished by an external pump.

17. A method for exchanging a used fluid with a fresh fluid in a vehicle having a transmission connected to a fluid circuit for conducting a circulated fluid therein in an operational direction, said used fluid initially being contained within said transmission and said fluid circuit, at least a substantial portion of which is subsequently discharged into a receptacle, said fresh fluid initially being contained in a source container, said method comprising the steps of:

providing a fluid exchange system having a first conduit for communicating fresh fluid to the transmission and a second conduit for communicating used fluid from the transmission, said fluid exchange system having a fluid flow alignment mechanism;

determining the direction of flow of the circulated fluid within the fluid circuit;

operating said fluid flow alignment mechanism to align the flow of the fresh fluid relative to the flow of the circulated fluid within the fluid circuit; and delivering a quantity of the fresh fluid sufficient to substantially replace the used fluid within the transmission and the fluid circuit from the source container into the transmission and the fluid circuit within the vehicle as the used fluid is expelled from the transmission and the fluid circuit into the receptacle at substantially equivalent volumetric flow rates.

18. A method for exchanging a used fluid with a fresh fluid in a vehicle having a transmission connected to a fluid circuit for conducting a circulated fluid therein in an operational direction, said used fluid initially being contained within said transmission and said fluid circuit, at least a substantial portion of which is subsequently discharged into a receptacle, said fresh fluid initially being contained in a source container, said method comprising the steps of:

providing a fluid exchange system having a first conduit for communicating fresh fluid to the transmission and a second conduit for communicating used fluid from the transmission, said first conduit and said second conduit each having an associated quick coupling assembly;

coupling the first conduit to the fluid circuit at a first location via the associated quick coupling assembly;

coupling the second conduit to the fluid circuit at a second location via the associated quick coupling assembly;

determining the direction of flow of the circulated fluid within the fluid circuit;

uncoupling the first conduit at the first location and uncoupling the second conduit at the second location;

coupling the first conduit at the second location and coupling the second conduit at the first location to align the flow of the fresh fluid relative to the flow of the circulated fluid within the fluid circuit; and delivering a quantity of the fresh fluid sufficient to substantially replace the used fluid within the transmission and the fluid circuit from the source container into the transmission and the fluid circuit within the vehicle as the used fluid is expelled from the transmission and the fluid circuit into the receptacle at substantially equivalent volumetric flow rates.

19. A fluid exchange system for use in exchanging a used fluid with a fresh fluid in a vehicle having an automatic transmission and a fluid cooling circuit operatively connected to conduct a circulated fluid therein, said transmission having a dipstick filler tube, said fresh fluid being contained in and dispensed from a source external to said vehicle, said used fluid initially being contained within said vehicle and discharged into a receptacle external to said vehicle, said fluid exchange system comprising;

a first fluid line intercoupled to the fluid exchange system, the source, and the fluid cooling circuit to conduct fresh fluid from the source into the fluid cooling circuit, said conducted fresh fluid having a first fluid flow rate;

a second fluid line intercoupled to the fluid exchange system and the fluid cooling circuit to conduct used fluid from the cooling circuit, said used fluid having a second fluid flow rate;

a pump operatively coupled to the second fluid line for assisting in an extraction of used fluid from the cooling circuit; and a control assembly operatively coupled to the first fluid line or the second fluid line to substantially balance the first fluid flow rate with the second fluid flow rate during an exchange procedure.

20. A method for exchanging a used fluid with a fresh fluid in a vehicle having a transmission connected to a fluid circuit for conducting a circulated fluid therein in an operational direction, said used fluid initially being contained within said transmission and said fluid circuit, at least a substantial portion of which is subsequently discharged into a receptacle, said fresh fluid initially being contained in a source container, said method comprising the steps of:

providing a fluid exchange system having a first conduit for communicating fresh fluid to the transmission and a second conduit for communicating used fluid from the transmission, said fluid exchange system having a fluid flow alignment mechanism;

determining the direction of flow of the circulated fluid within the fluid circuit;

operating said fluid flow alignment mechanism to align the flow of the fresh fluid relative to the flow of the circulated fluid within the fluid circuit; and delivering a quantity of the fresh fluid sufficient to substantially replace the used fluid within the transmission and the fluid circuit from the source container into the transmission and the fluid circuit within the vehicle as the used fluid is expelled from the transmission and the fluid circuit into the receptacle at substantially equivalent volumetric flow rates.

21. A method for using a fluid exchange system for exchanging a used fluid with a fresh fluid in a vehicle having an automatic transmission and a fluid cooling circuit operatively connected to conduct a circulated fluid therein, said transmission having a dipstick filler tube, said fresh fluid being contained in and dispensed from a source external to said vehicle, said used fluid initially being contained within said vehicle and discharged into a receptacle external to said vehicle, said method comprising the steps of:

providing a first fluid line fluidly coupling the fluid exchange system, the source, the fluid cooling circuit, and transmission dipstick filler tube to conduct fresh fluid from the source into both the fluid cooling circuit and the dipstick filler tube, said conducted fresh fluid having a first fluid flow rate, providing a second fluid line interconnected to the fluid exchange system and the vehicle to conduct the used fluid from the vehicle, said used fluid having a second fluid flow rate; and providing a control assembly operatively coupled to the first fluid line or the second fluid line to substantially balance the first fluid flow rate with the second fluid flow rate during an exchange procedure.

22. A method for using a fluid exchange system for exchanging a used fluid with a fresh fluid in a vehicle having an automatic transmission and a fluid cooling circuit operatively connected to conduct a circulated fluid therein, said transmission having a dipstick filler tubes said fresh fluid being contained in and dispensed from a source external to said vehicle, said used fluid initially being contained within said vehicle and discharged into a receptacle external to said vehicle, said method comprising the steps of:

providing a first fluid line fluidly coupling the fluid exchange system, the source, the fluid cooling circuit, and transmission dipstick filler tube to conduct fresh fluid from the source into both the fluid cooling circuit and the dipstick filler tube, said conducted fresh fluid having a first fluid volume;

providing a second fluid line interconnected to the fluid exchange system and the vehicle to conduct the used fluid from the vehicle, said used fluid having a second fluid volume; and providing a control assembly operatively coupled to the first fluid line or the second fluid line to substantially balance the first fluid volume with the second fluid volume upon completion of an exchange procedure.

23. The method of claim 22 wherein the first fluid line and the second fluid line are simultaneously interconnected to the vehicle.

24. A method of using a fluid exchange system for exchanging a used fluid with a fresh fluid in a vehicle having an automatic transmission and a fluid cooling circuit operatively connected to conduct a circulated fluid therein, said transmission having a dipstick filler tube, said fresh fluid being contained in and dispensed from a source external to said vehicle, said used fluid initially being contained within said vehicle and discharged into a receptacle external to said vehicle, said method comprising the steps of:

providing a first fluid line intercoupled to the fluid exchange system, the source, and the fluid cooling circuit to conduct fresh fluid from the source into the fluid cooling circuit;

providing a second fluid line intercoupled to the fluid exchange system, the fluid cooling circuit, and the dipstick filler tube to conduct used fluid from both the cooling circuit and the dipstick filler tube;

providing a pump assembly operatively coupled to the second fluid line, operating the pump assembly to extract used fluid from the cooling circuit or the dipstick filler tube; and providing a control assembly operatively coupled to the first fluid line or the second fluid line to substantially balance a volume of fresh fluid with a volume of used fluid upon completion of an exchange procedure.

25. The method of using the exchange system of claim 24 further comprising the step of:

operating the vehicle to operate a transmission pump during at least a portion of the exchange procedure.

26. In a machine for exchanging used fluid from an automotive automatic transmission with fresh fluid, said machine comprising:

a source of fresh fluid;

a pump unit flowing fresh fluid from the source to the automatic transmission; and a flow alignment device including four fluid ports, each of said four ports being in direct fluid flow communication with at least one other of said four ports, two of said ports being bi-directional ports which may receive used fluid from the transmission or send fresh fluid to said transmission, and a different two of said ports being respectively an inflow port at which said machine receives used fluid from the transmission and an outflow port to which the machine delivers new fluid, said flow alignment device having at least one valve assembly for communicating used fluid or fresh fluid within the flow alignment device.

27. The machine of claim 26 wherein the flow alignment device includes a single valve body and each of said four ports being in direct fluid flow communication with only one other of said four ports.

28. The machine of claim 26 wherein the valve assembly is responsive to a pressure of the used fluid.

29. The machine of claim 26 wherein the valve assembly is manually biased by an operator during an exchange procedure.

30. The machine of claim 26 wherein the valve assembly is controlled by an electronic control system.

31. A method of exchanging used fluid with a fresh fluid in an automotive automatic transmission having an internal pump and an external fluid circulation loop, said method comprising steps of:

providing a volume of fresh fluid;

providing a pump unit flowing fresh fluid from a source to the automatic transmission; and providing a flow alignment device including four fluid ports, each of said four ports being in direct fluid flow communication with at least one other of said four ports, two of said ports being bi-directional ports which may receive used fluid from the transmission or send fresh fluid to said transmission, and a different two of said ports being respectively an inflow port at which said machine receives used fluid from the transmission and an outflow port to which the machine delivers new fluid, said flow alignment device having at least one valve assembly for communicating used fluid or fresh fluid within the flow alignment device.

32. The method of claim 31 wherein the flow alignment device includes a single valve body and each of said four ports being in direct fluid flow communication with only one other of said four ports.

33. The method of claim 31 wherein the valve assembly is responsive to a pressure of the used fluid.

34. The method of claim 31 wherein the valve assembly is manually biased by an operator during an exchange procedure.

35. The method of claim 31 wherein the valve assembly is controlled by an electronic control system.

* * * * *

UNITED STATES PATENT AND TRADEMARK OFFICE
CERTIFICATE OF CORRECTION

PATENT NO.      : 6,330,934 B1                                                      Page 1 of 1
DATED           : December 18, 2001
INVENTOR(S)     : James P. Viken It is certified that error appears in the above-identified patent and that said Letters Patent is
hereby corrected as shown below:

<u>Title page,</u>
Item [63], should read as follows:

-- Continuation of application Ser. No. 08/469,673, filed June 6, 1995, and a
continuation-in-part of application No. 08/209,061, filed on March 9, 1994, now
Pat. No. 5,472,064, and now U.S. Reissue Pat. No. RE36,650, which is a
continuation-in-part of application No. 07/781,322, filed Oct. 23, 1991, and now
Pat. No. 5,318,080. --

<u>Column 1,</u>
Lines 4 - 9 be amended as follows:

-- This application is a continuation of application Ser. No. 08/469,673, filed
June 6, 1995, and is a continuation-in-part of application Ser. No. 08/209,061 filed
March 9, 1994, now granted U.S. Pat. No. 5,472,064, and now U.S. Reissue Pat.
No. RE36,650, which was a continuation-in-part of application Ser. No. 07/781,322
filed Oct. 23, 1991, and now U.S. Pat. No. 5,318,080. --

Signed and Sealed this

Fourth Day of February, 2003

JAMES E. ROGAN
*Director of the United States Patent and Trademark Office*